United States Patent [19]

Sarantakis

[11] 4,081,433
[45] Mar. 28, 1978

[54] D-Nle⁴-SOMATOSTATIN AND ANALOGUES THEREOF

[75] Inventor: Dimitrios Sarantakis, West Chester, Pa.

[73] Assignee: American Home Products Corporation, New York, N.Y.

[21] Appl. No.: 759,203

[22] Filed: Jan. 13, 1977

[51] Int. Cl.² .................. C07C 103/52; A61K 37/00
[52] U.S. Cl. ........................ 260/112.5 S; 424/177
[58] Field of Search ................................ 260/112.5 S

[56] References Cited
PUBLICATIONS

Lippmann et al.; Experitentia 32, 1976, pp. 1034–1036.

*Primary Examiner*—Delbert R. Phillips
*Attorney, Agent, or Firm*—Richard K. Jackson

[57] ABSTRACT

Polypeptides of the formula:

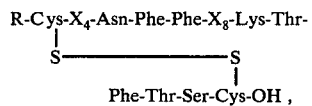

the linear precursors, intermediates and non-toxic acid addition salts thereof, wherein R is hydrogen or Ala—Gly;
$X_4$ is D—Nle, D—Val, D—Phe, D—Tyr or D—Trp; and
$X_8$ is L—Trp or D—Trp are described. These polypeptides inhibit the secretion of growth hormone.

9 Claims, No Drawings

D-Nle⁴-SOMATOSTATIN AND ANALOGUES THEREOF

DESCRIPTION OF THE INVENTION

In accordance with this invention there is provided a group of polypeptides of the following formula:

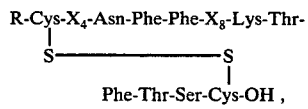

the linear precursors, intermediates and non-toxic acid addition salts thereof, in which R is hydrogen or Ala—Gly, $X_4$ is D—Nle, D—Val, D—Phe, D—Tyr or D—Trp; and $X_8$ is L—Trp or D—Trp. These compounds inhibit the secretion of growth hormone and the like somatostatin are useful in the treatment of diabetes mellitis and acromegaly.

The intermediates produced in the synthesis of the polypeptides disclosed herein present an additional aspect of the invention. The intermediates are of the formula:

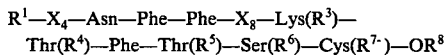

wherein
$X_4$ is D—Nle, D—Val, D—Phe, D—Tyr($R^2$) or D—Trp;
$X_8$ is L—tryptophyl or D—tryptophyl;
$R^1$ is hydrogen or an α-amino protecting group;
$R^2$ is hydrogen, benzyl, 2,6-dichlorobenzyl, benzyloxycarbonyl or 2-bromobenzyloxycarbonyl;
$R^3$ is hydrogen, tosyl, t-amyloxycarbonyl, t-butyloxycarbonyl, diisopropyloxycarbonyl, benzyloxycarbonyl; halobenzyloxycarbonyl or nitrobenzyloxycarbonyl;
$R^4$, $R^5$, and $R^6$ are hydrogen or, independently, acetyl, benzoyl, tert-butyl, benzyl;
$R^7$ is benzyl, trityl, benzyloxycarbonyl, benzhydryl, tetrahydropyranyl, acetamidomethyl, benzoyl, benzylthiomethyl, ethylcarbamoyl, thioethyl, S-sulfonate salt, 3,4-dimethylbenzyl, p-methoxybenzyl or p-nitrobenzyl; and
$R^8$ is hydrogen or —CH₂—[polystyrene resin support]

The polypeptide intermediates and final products are produced by the well known solid phase method as described by Stewart et al., Solid Phase Peptide Synthesis, Freeman and Co., San Francisco, 1969. As applied to the compounds of this invention, α-amino and sulfhydryl protected cysteine is attached to a chloromethylated polystyrene resin followed by removal of the α-amino protecting group with trifluoroacetic acid in methylene chloride, trifluoroacetic acid alone or HCl in dioxane. The deprotection is conducted at a temperature between about 0° C. and room temperature. Other standard cleaving reagents and conditions for removal of specific α-amino protecting groups may be used as described in Schroder E. Lubke, "The Peptides", 1, 72–75 (Academic Press, 1965). After removal of the α-amino protecting group the subsequent protected amino acids are coupled individually to the resin supported sequence, seriatim. Alternatively, small peptide fragments may be prepared by the solution method and introduced into the solid phase reactor in the desired order. Each protected amino acid or amino acid sequence is introduced into the solid phase reactor in about a four fold excess. The coupling is carried out in dimethylformamide, methylene chloride, or a mixture of the two solvents. The success of each coupling reaction at each stage of the synthesis is determined by the ninhydrin reaction as described by E. Kaiser et al., Analyt. Biochem., 34, 595(1970). Where incomplete coupling has occurred, the reaction is repeated before the α-amino protecting group is removed for introduction of the next amino acid or amino acid sequence. The coupling reagents employed were 1-hydroxybenzotriazole and diisopropylcarbodiimide.

After the desired amino acid sequence has been synthsized, the polypeptide is removed from the resin support by treatment with hydrogen fluoride and anisole to obtain the fully deprotected linear polypeptide. The cyclic disulfide is produced by air oxidation.

Non-toxic acid addition salts of the linear and cyclic polypeptides are produced by methods well known in the art from hydrochloric, hydrobromic, sulfuric, phosphoric, polyphosphoric, maleic, acetic, citric, benzoic, succinic, malonic or ascorbic acid and the like.

The protecting groups employed throughout the solid phase synthesis are well known to the art. The α-amino protecting groups employed with each amino acid introduced in sequence of the ultimate polypeptide are of the (1) acyl type protecting groups illustrated by the following: formyl, trifluoroacetyl, phthalyl, p-toluenesulfonyl (tosyl), nitrophenylsulfenyl, etc.; (2) aromatic urethane type protecting groups illustrated by benzylocycarbonyl and substituted benzyloxycarbonyl such as p-chlorobenzyloxycarbonyl, p-nitrobenzyloxycarbonyl, p-bromobenzyloxycarbonyl, p-methoxybenzyloxycarbonyl; (3) aliphatic urethane protecting groups illustrated by tert-butyloxycarbonyl, diisopropylmethoxycarbonyl, isopropyloxycarbonyl, allyloxycarbonyl, 2,2,2-trichloroethoxycarbonyl, amyloxycarbonyl; (4) cycloalkyl urethane type protecting groups illustrated by cyclopentyloxycarbonyl, adamantyloxycarbonyl, cyclohexyloxycarbonyl; (5) thio urethane type protecting groups such as phenylthiocarbonyl; (6) alkyl type protecting groups as illustrated by triphenylmethyl (trityl); (7) trialkylsilane groups such as trimethylsilane. The preferred α-amino protecting group defined by $R^1$ is tert-butyloxycarbonyl.

Protection for the phenolic hydroxyl group, depicted as $R^2$ when $X_4$ is D-tyrosyl, may be by benzyl, 2,6-dichlorophenyl, benzyloxycarbonyl, 2-bromobenzyloxycarbonyl and the like.

Protection for the side chain amino group of lysine, depicted as $R^3$, may be by tosyl, t-amyloxycarbonyl, t-butyloxycarbonyl, diisopropyloxycarbonyl, benzyloxycarbonyl, halobenzyloxycarbonyl, nitrobenzyloxycarbonyl, and the like, the 2-chlorobenzyloxycarbonyl group being preferred.

Protection for the hydroxyl group of threonine and serine as depicted by $R^4$, $R^5$, and $R^6$, may be with the acetyl, benzoyl, tert-butyl, benzyl. The benzyl group is preferred for this purpose.

The protecting group for the sulfhydryl group of the cysteinyl amino acid residue illustrated by $R^7$ is a group selected from the class consisting of benzyl; substituted benzyl wherein the substituent is at least one of methyl, methoxy, nitro, or halo (e.g. 3,4-dimethylbenzyl, p-methoxybenzyl, p-chlorobenzyl, p-nitrobenzyl, etc); trityl, benzyloxycarbonyl, benzhydryl, p-methoxybenzyloxycarbonyl, benzylthiomethyl, ethylcarbamoyl, thioethyl, tetrahydropyranyl, acetamidomethyl, benzoyl, s-sulfonate salt, etc; the p-methoxybenzyl group being preferred.

In selecting a particular side chain protecting group to be used in the synthesis of the peptides of this invention, the following rules should be followed: (a) The side chain protecting group must be stable to the reagent and under the reaction conditions selected for removing the α-amino protecting group at each step of the synthesis, (b) the protecting group must retain its protecting properties (i.e. not be split off under coupling conditions), and (c) the side chain protecting group must be removable upon the completion of the synthesis containing the desired amino acid sequence under reaction conditions that will not alter the peptide chain.

The following Example illustrates the preparative technique applicable in the production of the compounds of this invention. By introducing tert-butyloxycarbonyl protected D-tryptophan into the solid phase reactor as the seventh amino acid introduced, the compounds corresponding to D-Trp as $X_8$ in the generic formula, supra, are produced. Similarly by introducing tert-butyloxycarbonyl protected D-valine, D-phenylalanine, D-tyrosine(O-2,6-dichlorobenzyl) or D-tryptophan into the solid phase reactor as the eleventh amino acid in lieu of the illustrated D-norleucine, there is obtained the corresponding polypeptide varied in the 4-position. The fully protected intermediate containing the $D-Trp^8$ and $D-Nle^4$ units, corresponding to the illustrative compound prepared in the following example is:

tert-butyloxycarbonyl-L-alanyl-glycyl-S-p-methoxybenzyl-L-cysteinyl-D-norleucyl-L-asparaginyl-L-phenylalanyl-L-phenylalanyl-D-tryptophyl-ε-2-chlorobenzyloxycarbonyl-L-lysyl-O-benzyl-L-threonyl-L-phenylalanyl-O-benzyl-L-threonyl-O-benzyl-L-seryl-S-p-methoxybenzyl-L-cysteinyl-hydroxymethyl-polystyrene.

Likewise, by omitting the sequential introduction of t-butyloxycarbonyl-Gly-OH as the thirteenth amino acid and t-butyloxycarbonyl-Ala-OH as the fourteenth member of the sequence affords, after complete deprotection, a dodecapeptide of the formula:

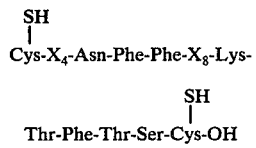

in which $X_4$ is D—Nle, D—Val, D—Phe, D—Tyr or D—Trp and $X_8$ is L—Trp or D—Trp and all undesignated optically active amino acids are of the L-series, which linear intermediate is readily cyclized under mild air oxidation.

EXAMPLE I tert-Butyloxycarbonyl-L-alanyl-glycyl-S-p-methoxybenzyl-L-cysteinyl-D-norleucyl-L-asparaginyl-L-phenylalanyl-L-phenylalanyl-L-tryptophyl-ε-2-chlorobenzyloxycarbonyl-L-lysyl-O-benzl-L-threonyl-L-phenylalanyl-O-benzyl-Lthreonyl-O-benzyl-L-seryl-S-p-methoxybenzyl-L-cysteinyl-hydroxymethyl-polystyrene ester Chloromethylated polystyrene resin 1% cross linked with divinyl benzene (Lab Systems, Inc.) was esterified with Boc-Cys(SMBzl)-OH according to Gisin, *Helv. Chim. Acta* 56, 1976 (1973). The polystyrene resin ester was treated according to schedule A for the incorporation of Boc-Ser(Bzl)-OH, Boc-Thr(Bzl)-OH, Boc-Phe-OH, Boc-Thr(Bzl)-OH, Boc-Lys(Clz)-OH, Boc-Trp-OH, Boc-Phe-OH, Boc-Phe-OH, Boc-Asn-OH, Boc-D-Nle-OH, Boc-Cys(SMBzl)-OH and Boc-Ala-Gly-OH to afford the title peptidoresin.

Schedule A

1. Wash with $CH_2Cl_2 \times 3$
2. Treat with $TFA-CH_2Cl_2$-EDT (1:1:5%) for 5 min.
3. Treat with TFA $CH_2Cl_2$-EDT (1:1:5%) for 25 min.
4. Wash with $CH_2Cl_2 \times 3$
5. Wash with DMF
6. Treat with 12% TEA in DMF twice for 3 min.
7. Wash with DMF
8. Wash with $CH_2Cl_2 \times 3$
9. Treat with 4 equivalents of the corresponding amino acid derivative in $CH_2Cl_2$-DMF and 4 equivalents of N-hydoxybenzotriazole and stir for 5 min. In the case of asparagine 8 equivalents of N-hydoxybenzotriazole were added.
10. Add in two portions 5 equivalents of DIC dissolved in $CH_2Cl_2$ and over a period of 30 minutes. Reaction time 12–18 hours.
11. Wash with DMF $\times$ 3
12. Wash with $CH_2Cl_2 \times 3$
13. Test ninhydrin reaction according to Kaiser et al., *Annal. Biochem.* 34, 595 (1970). In case of incomplete reaction repeat lines 9 to 13 as above.

EXAMPLE 2

L-Alanyl-glycyl-L-cysteinyl-D-norleucyl-L-asparaginyl-L-phenylalanyl-L-phenylalanyl-L-tryptophyl-L-lysyl-L-threonyl-L-phenylalanyl-L-threonyl-L-seryl-L-cysteine cyclc (1→14) disulfide The peptidoresin of the previous example (13 g.) was mixed with 20 ml. anisole and treated with liquid HF for 45 minutes. The excess liquid HF was distilled in vacuo as fast as possible and the residue was extracted with dearated 2M- aq. AcOH. The aqueous solution was washed with diethyl ether and then evaporated to dryness in a rotary evaporator. The residue was dissolved in 4 liters of dearated water, the pH was adjusted to 7.4 and the solution was left to stand in the open air and in the cold for 3 days. The pH was adjusted to 6.4 and the solution was lyphilized to afford a white solid, 241 mg. Part of this solid was applied onto a column (2.5 × 150 cm) of Sephadex G-25 and eluted with 2M-aq. AcOH. $R_f$(n-butanol-water-gl. AcOH, 4:5:1)0.55
$R_f$(n-butanol-water-gl. AcOH-pyridine, 30:24:6:20)0.70
Amino-acid analysis: Asp (1) 0.95, Thr (2) 1.96, Ser (1) 0.89, Gly (1) 1.29, Ala (1) 1.14, Nle (1) factor not available for quantitative determination, Phe (3) 2.88, Lys (1) 1 $NH_3$ (1) 2.29, Trp (1) 0.67, Cys (2) N.D.

The activity of the product of the preceding preparatory example, $(D-Nle^4)$Somatostatin, was determined by the following procedure:

Albino male rats were administered Nembutal intraperitoneally at a dose of 50 milligrams per kilogram. Fifteen minutes later a subcutaneous injection of the test compound or physiological saline was administered. Ten minutes later 0.5 milliliters of arginine (300 millligrams per milliliter, pH 7.2) is injected into the heart. Five minutes after receipt of the arginine the rats are decapitated and blood is collected into trasylol-EDTA. An appropriate aliquot was assayed for growth hormone revealing a reduction of growth hormone to 83±23 ng/ml (p<0.05) compared to the control value of 208±52 ng/ml at a dose of 1 mg/kg. Thus, (D-Nle[4])Somatostatin, representative of the corresponding D-Val[4], D-Phe[4], D-Tyr[4] and D-Trp analogues as well as their (des-Ala[1]-Gly[2])somatostatin analogues and the corresponding D-Trp[8] analogues, is an effective agent for reducing secretion of growth hormone. Each of the compounds of this invention possess a functionally characterizing hydrophobic side chain grouping on the amino acid moiety in 4-position, which distinguishes them from polypeptides having hydrophilic groupings on the 4-amino acid.

The compounds described herein may be administered to warm blooded mammals, including humans, either intravenously, subcutaneously, intramuscularly or orally to inhibit the release growth hormone where the host being treated requires thereapeutic treatment for excess secretion of somatotropin which is associated with conditions such as juvenile diabetes and acromegaly. The required dosage will vary with the particular condition being treated, the severity of the condition and the duration of treatment. If the active ingredient is administered in tablet form the tablet may contain: a binder such as gum tragacanth, corn starch, gelatin, and excipient such as dicalcium phosphate; a disintegrating agent such as corn starch, alginic acid, etc.; a lubricant such as magnesium stearate; and a sweetening and/or flavoring liquid carriers for intravenous administration include isotonic saline, phosphate buffer solutions, etc.

What is claimed is:

1. A polypeptide of the formula:

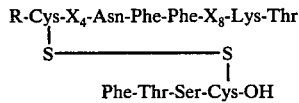

its linear precursor or a non-toxic acid addition salt thereof, in which

R is hydrogen or Ala—Gly—;

$X_4$ is D—Nle, D—Val, D—Phe, D—Tyr or D—Trp; and $X_8$ is L—Trp or D—Trp.

2. A polypeptide of claim 1 of the formula:

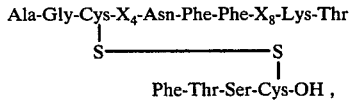

its linear precursor or a non-toxic acid addition salt thereof, in which $X_4$ is D—Nle, D—Val, D—Phe, D—Tyr or D—Trp and $X_8$ is L—Trp or D—Trp.

3. A polypeptide of claim 1 of the formula:

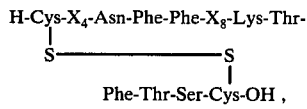

its linear precursor or a non-toxic acid addition salt thereof, in which $X_4$ is D—Nle, D—Val, D—Phe, D—Tyr or D—Trp and $X_8$ is L—Trp or D—Trp.

4. The polypeptide of claim 2 which is L-Ala-Gly-L-cysteinyl-D-norleucyl-L-asparaginyl-L-phenylalanyl-L-phenylalanyl-L-tryptophyl-L-lysyl-L-threonyl-L-phenylalanyl-L-threonyl-L-seryl-L-cysteine or a non-toxic acid addition salt thereof.

5. The polypeptide of claim 2 which is L-Ala-Gly-L-cysteinyl-D-norleucyl-L-asparaginyl-L-phenylalanyl-L-phenylalanyl-L-tryptophyl-L-lysyl-L-threonyl-L-phenylalanyl-L-threonyl-L-seryl-L-cysteine (cyclic 1,12 disulfide) or a non-toxic acid addition salt thereof.

6. A polypeptide of the formula:

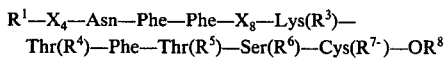

wherein $X_4$ is D-norleucyl, D-valyl, D-phenylalanyl, D-tyrosyl($R^2$) or D-tryptophyl;

$X_8$ is L-tryptophyl or D-tryptophyl;

$R^1$ is hydrogen or an α-amino protecting group;

$R^2$ is hydrogen, benzyl, 2,6-dichlorobenzyl, benzyloxycarbonyl or 2-bromobenzyloxycarbonyl;

$R^3$ is hydrogen, tosyl, t-amyloxycarbonyl, t-butyloxycarbonyl, diisopropyloxycarbonyl, benzyloxycarbonyl, halobenzyloxycarbonyl or nitrobenzyloxycarbonyl;

$R^4$, $R^5$ and $R^6$ are hydrogen or, independently, acetyl, benzoyl, tert-butyl, benzyl;

$R^7$ is benzyl, trityl, benzyloxycarbonyl, benzhydryl, tetrahydropyranyl, acetamidomethyl, benzoyl, benzylthiomethyl, ethylcarbamoyl, thioethyl, S-sulfonate salt, 3,4-dimethylbenzyl, p-methoxybenzyl or p-nitrobenzyl; and $R^8$ is hydrogen or —$CH_2$—[polystyrene resin support]

7. A polypeptide of claim 6 in which $R^1$ is tert-butyloxycarbonyl.

8. A polyppeptide of claim 6 in which $R^1$ is hydrogen.

9. A polypeptide of claim 6 in which $X_4$ is D-Nle;

$X_8$ is L-Trp;

$R^1$ is tert-butyloxycarbonyl;

$R^3$ is 2-chlorobenzyloxycarbonyl;

$R^4$, $R^5$, and $R^6$ are benzyl;

$R^7$ is p-methoxybenzyl; and $R^8$ is —$CH_2$—[polystyrene resin support].

* * * * *